(12) United States Patent
Bordoloi et al.

(10) Patent No.: US 7,129,068 B2
(45) Date of Patent: Oct. 31, 2006

(54) **PROCESS FOR THE ISOLATION OF POLYHYDROXYBUTYRATE FROM *BACILLUS MYCOIDES* RLJ B-017**

(75) Inventors: Manobjyoti Bordoloi, Jorhal (IN); Bornali Borah, Jorhal (IN); Purbali S. Thakur, Jorhal (IN); Jagdish Narayan Nigam, Jorhal (IN)

(73) Assignee: Council of Scientific and Industrial Research, New Delhi (IN)

( * ) Notice: Subject to any disclaimer, the term of this patent is extended or adjusted under 35 U.S.C. 154(b) by 307 days.

(21) Appl. No.: 10/613,532

(22) Filed: Jul. 3, 2003

(65) Prior Publication Data

US 2004/0191878 A1    Sep. 30, 2004

(51) Int. Cl.
| | |
|---|---|
| *C12P 7/62* | (2006.01) |
| *C12P 7/42* | (2006.01) |
| *C08G 63/82* | (2006.01) |
| *C08G 63/87* | (2006.01) |
| *C08G 63/78* | (2006.01) |

(52) U.S. Cl. .................... 435/135; 528/271; 528/274

(58) Field of Classification Search ................. 435/135
See application file for complete search history.

(56) References Cited

U.S. PATENT DOCUMENTS

| | | |
|---|---|---|
| 5,191,037 A | 3/1993 | Doi et al. |
| 5,371,002 A | 12/1994 | Dennis et al. |
| 6,190,879 B1 | 2/2001 | Bech |

*Primary Examiner*—Herbert J. Lilling
(74) *Attorney, Agent, or Firm*—Ladas and Parry LLP

(57) ABSTRACT

The present invention describes a process for the isolation of polyhydroxybutyrate of the formula 1

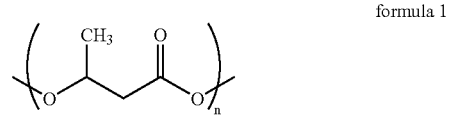

formula 1 by growing a culture of *Bacillus mycoides* RLJ B-017 in a growth medium and a carbon source selected from sucrose, molasses and pineapple waste.

14 Claims, 2 Drawing Sheets

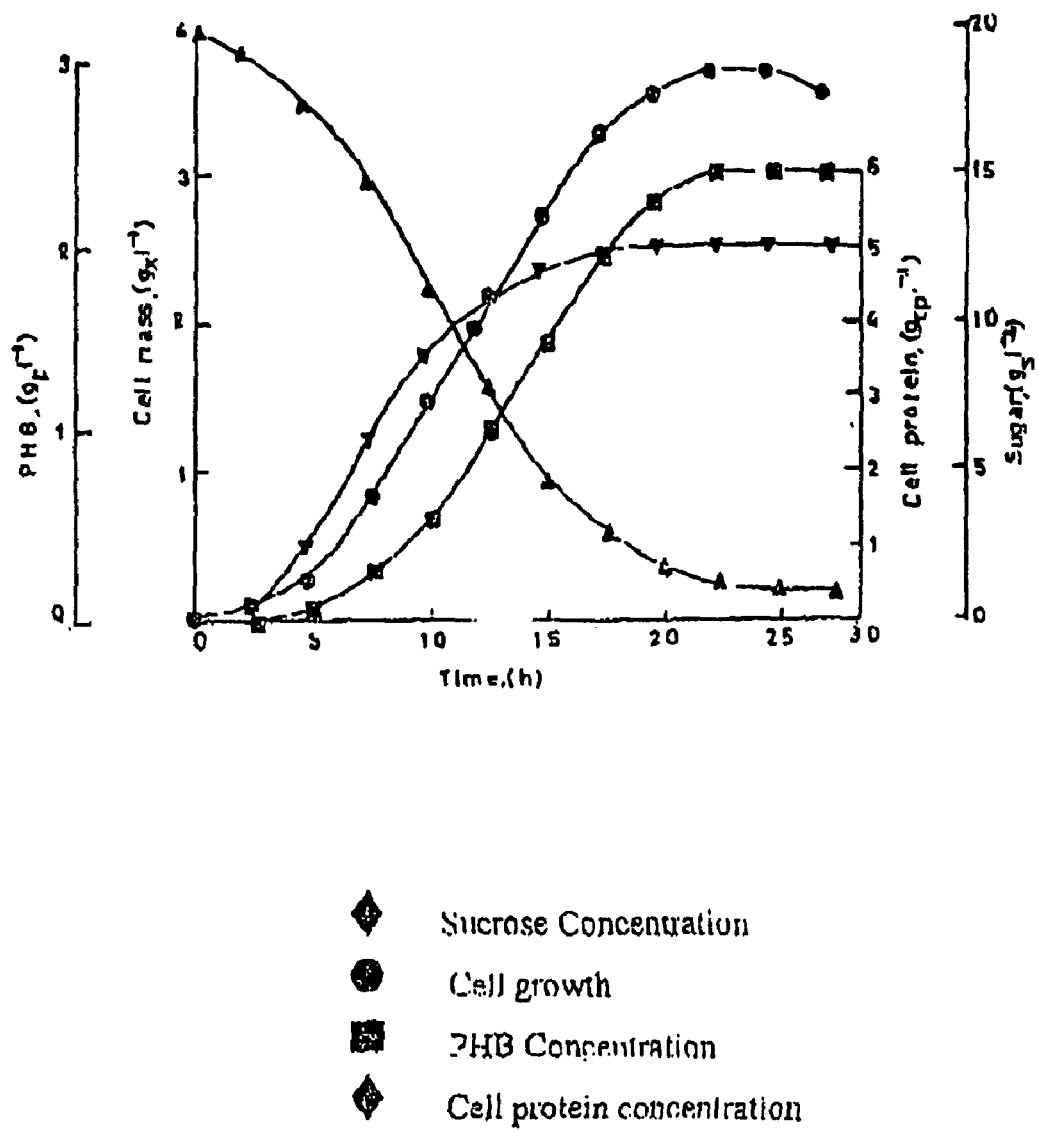
♦ Sucrose Concentration
● Cell growth
▨ PHB Concentration
♦ Cell protein concentration
Fig1. : Batch fermentation production curves of *B. mycoides* RLJ H-017 grown on 20 g/litre sugar (sucrose) and

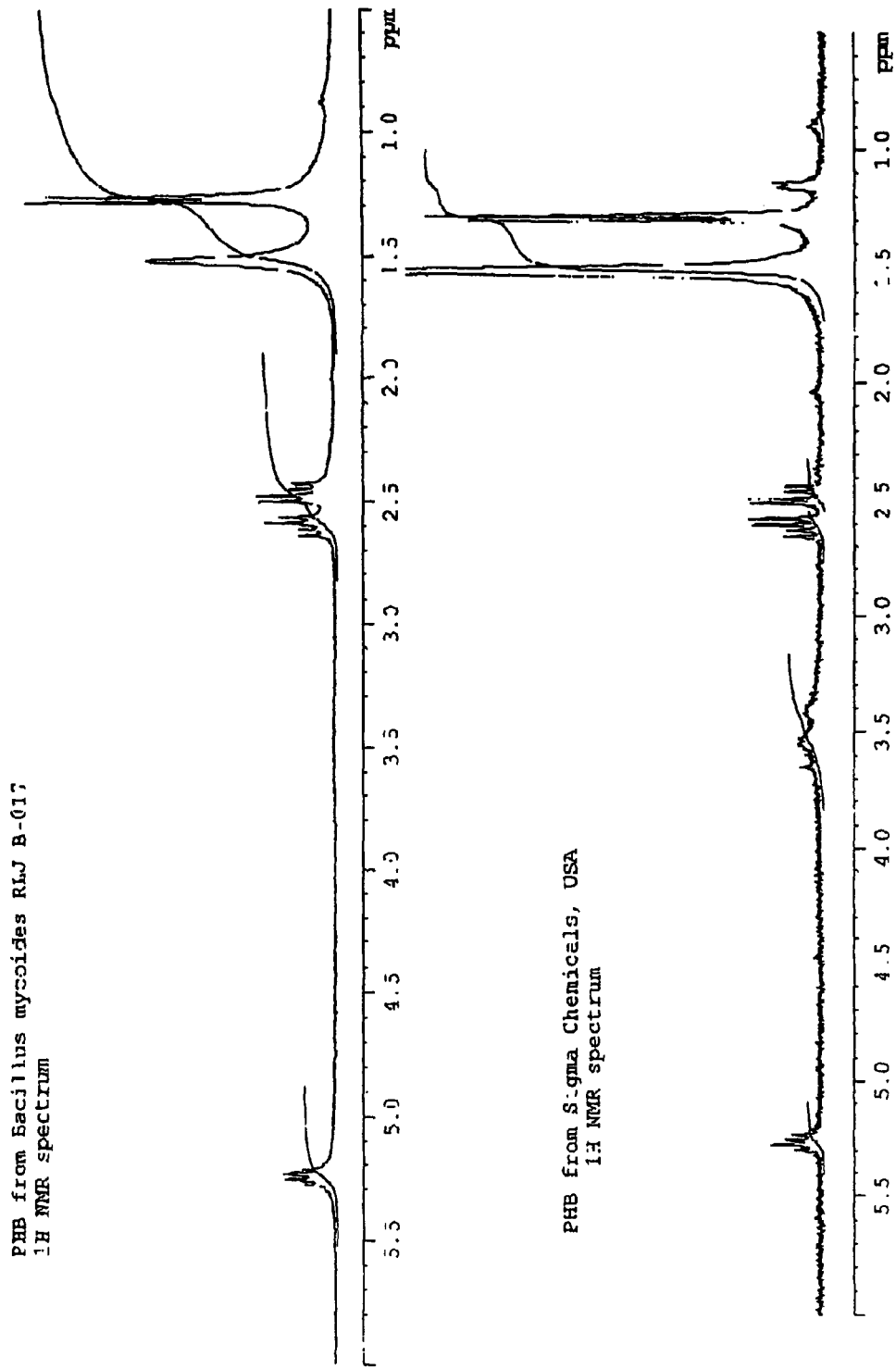
Figure 2 : Comparison of the 1H NMR spectra of PHB produced by Bacillus mycoides RLJ B-017 with sucrose/molasses as carbon source with that of M/S Sigma Chemicals, USA

PROCESS FOR THE ISOLATION OF POLYHYDROXYBUTYRATE FROM *BACILLUS MYCOIDES* RLJ B-017

FIELD OF THE INVENTION

The present invention relates to a process for the isolation of polyhydroxybutyrate from *Bacillus mycoides* RLJ B-017. More particularly, the present invention relates to a process for the recovery of a polyhydroxybutyrate of the formula 1

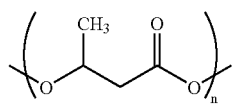

formula 1 from *Bacillus mycoides* RLJ B-017 by using sucrose, molasses, pine apply waste, etc. as the carbon source.

BACKGROUND OF THE INVENTION

Commodity polymers are typically produced from petrochemical sources by well-known synthetic means. However, recent advances in technology have resulted in the promise of new sources of commodity polymers. Particularly promising is the production of plastic resins using living organisms ("bioplastic" or Biopol), including bacteria to produce polymers such as polyhydroxyalkanoate (PHA); a number of bacteria which naturally produce PHA are also promising sources of PHA. (see for example, NOVEL BIODEGRADABLE MICROBIAL POLYMERS, E. A. Dawes, ed., NATO ASI Series, Series E: Applied Sciences—Vol. 186, Kluwer Academic Publishers (1990); Poirier, Y., D. E. Dennis, K. Klomparens and C. Somerville, "Polyhydroxybutyrate, a biodegradable thermoplastic produced in transgenic plants", SCIENCE, Vol. 256, pp. 520–523 (1992). In a large scale production, for example agricultural production, isolation and culture of a new organism and cheap raw material for the production of bioplastic is a critical step for determining the practical feasibility of such technology.

PHB is an energy storage material produced by a variety of bacteria in response to environmental stress and is a homopolymer of D-(-)-3-hydroxybutyrate of the formula 1 which has properties comparable to polypropylene. Because PHB is biogdegradable, there is considerable interest in using PHB for packaging purposes as opposed to other plastic materials in order to reduce the environmental impact of human garbage. PHB also has utility in antibiotics, drug delivery, medical suture and bone replacement applications. PHB is commercially produced from *Alcaligenes eutrophus* and sold under the trade name Biopol.

As described above and by Slater et al, in "Cloning and Expression in *Escherichia coli* of the *Alcaligenes eutrophus* H16 Poly-beta-Hydroxybutyrate Biosynthetic Pathway", Journal of Bacteriology, Vol 170, No. 10, Oct., 1988, p. 4431–4436, which is also incorporated herein by reference, it was shown that *E. coli* could be genetically transformed with genes from *A. eutrophus* which code for the PHB biosynthetic pathway. *E. coli* are a far better vehicle for producing PHB than *A. eutrophus* since more is known about handling the bacteria, *E. coli*, i.e. *E. coli* is more easily controlled and manipulated. The transformed *E. coli* is able to express PHB in relatively large quantities.

Despite PHB's advantages over other materials, its high cost of production has hindered its performance in the market. Currently, PHB is produced in transformed *E. coli* by growing the *E. coli* on luria broth (LB) and using glucose as the carbon source.

Approximately one third of the production cost of PHB is attributable to the rich LB medium and the glucose. If a less expensive carbon source could be utilized, the overall cost of PHB production could be significantly reduced. In addition, much of the total cost of PHB production is attributable to purifying the PHB produced in the *E. coli*. Currently, PHB is purified by centrifugation, followed by mechanical lysis of the cells to release PHB, a high temperature procedure to agglomerate the PHB, and finally a spray drying step to procure to agglomerate the PHB, and finally a spray drying stop to procure the purified granules. If a less expensive method were available for collecting the PHB from a new organism of high efficiency together with the application of a cheap carbon source, the overall cost of PHB production could be significantly reduced.

In view of the above, there is a need for a simple and economical process for the production of bioplastics from a new biological source suing cheap raw materials. Such a process would preferably be easily adaptable as an integral part of the agricultural commercial production of bioplastics.

OBJECTS OF THE INVENTION

It is therefore an object of the present invention to provide a process for producing bioplastics from a biological source material.

It is therefore an object of the present invention to provide improved techniques for producing polyhydroxy butyrate of the structure 1 using a new bacteria, *Bacillus mycoides* RLJ B-017, and sucrose and molasses as cheap carbon source.

It is another object of this invention to provide a stain *Bacillus mycoides* RLJ B-017 which can accumulate PHB at higher levels than previous methods and which can utilize minimal medium containing sucrose for growing conditions.

It is another object of this invention to provide a strain *Bacillus mycoides* RLJ B-017 which can accumulate PHB at higher levels than previous methods and which can utilize minimal medium containing molasses for growing conditions.

It is yet another object of the invention to provide a economical and efficient process for the isolation of bioplastic polyhydroxybutyrate.

It is yet another object of this invention to provide a method of agglomerating PHB granules from lysed *Bacillus mycoides* RLJ B-017 cells using an solution sodium hypochlorite, calcium hypochlorite or any metal hypochlorite in chloroform or any polyhalogenated hydrocarbon solvent.

SUMMARY OF THE INVENTION

Accordingly the present invention provides a process for the isolation of polyhydroxybutyrate of the formula 1

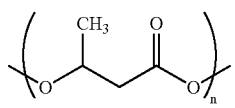

formula 1 said process comprising growing a culture of *Bacillus mycoides* RLJ B-017 in a growth medium and a carbon source selected from sucrose, molasses and pineapple waste for a time period of equal to or greater than twenty four hours, said bacterial host producing intra-cellular poly-beta-hydroxybutyrate of the structure 1, lysing said bacterial host in said culture to release said poly-betahydroxybutyrate of the structure 1, and separating the isolate of said poly-beta-hydroxybutyrate of the structure 1.

In one embodiment of the invention, the growth medium comprises (g $1^{-1}$): sucrose, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_47H_2O$, 0.01; and trace-element solution 1 ml $1^{-1}$ element solution comprising (g $1^{-1}$): $ZnSO_47H_2O$, 0.2; $H_3BO_3$, 0.6; $MnCl_2 4H_2O$, 0.06; $CoCl_2 6H_2O$, 0.4; $CuSO_44H_2O$, 0.02; $NaMoO_4.2H_2O$, 0.06. with pH 7.2.

In another embodiment of the invention, the growth medium comprises (g $1^{-1}$): molasses, 20; nutrient broth, 8; $KH_2PO_4$, 1.5; $(NH_4)_2SO_4$, 2.0; $Na_2HPO_4. 12H_2O$, 2.239; $MgSO_4.7H_2O$, 0.2; $CaCl_2.2H_2O$, 0.02; $FeSO_47H_2O$, 0.01; and trace-element solution 1 ml $1^{-1}$ said trace element solution comprising (g $1^{-1}$): $ZnSO_47H_2O$, 0.2; $H_3BO_3$, 0.6; $MnCl_2 4H_2O$, 0.06; $CoCl_2 6H_2O$, 0.4; $CuSO_44H_2O$, 0.02; $NaMoO_4.2H_2O$, 0.06. with pH 7.2.

In a further embodiment of the invention, the growth medium comprises (g $1^{-1}$): pineapple waste, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_47H_2O$, 0.01; and trace-element solution 1 ml $1^{-1}$ said trace element solution comprising (g $1^{-1}$): $ZnSO_47H_2O$, 0.2; $H_3BO_3$, 0.6; $MnCl_24H_2O$, 0.06; $CoCl_2 6H_2O$, 0.4; $CuSO_44H_2O$, 0.02; $NaMoO_4.2H_2O$, 0.06. with pH 7.2.

In a further embodiment of the invention, the polyhydroxybutyrate of formula 1 is separated from the culture of said organism and pelletised, the cell pellet thus obtained being treated with a ionic reagent comprising a dispersion of a metal hypochlorite in a halogenated hydrocarbon solvent, to agglomerate said poly-beta-hydroxybutyrate of the structure 1.

In yet another embodiment of the invention, the metal hypochlorite is selected from sodium hypochlorite and calcium hypochlorite.

In a further embodiment of the invention, the halogenated hydrocarbon solvent comprises chloroform.

In yet another embodiment of the invention, the concentration of said ionic reagent used is in the range of one molar to one millimolar.

In another embodiment of the invention, the polyhydroxytbutyrate of formula 1 is separated from the organism culture by centrifugation to obtain three separate phases, wherein the lower phase containing polyhydroxybutyrate of the structure 1 is dissolved in chloroform and precipitated by adding ethanol.

In a further embodiment of the invention, the precipitate is chilled and recovered by further centrifuging to obtain polyhydroxybutyrate of the structure 1.

BRIEF DESCRIPTION OF THE ACCOMPANYING DRAWINGS

FIG. 1 is a line graph showing PHB accumulation versus time in hours, consumption of sucrose versus time in hours; cell growth versus time in hours; cell protein concentration versus time in hours during accumulation of PHB by *Bacillus mycoides* RLJ B-017.

FIG. 2 is a comparison of the $^1H$, NMR spectra of PHB produced by *Bacillus mycoides* RLJ B-017 with that of obtained from Sigma Chemicals USA.

DETAILED DESCRIPTION OF THE INVENTION

According to the invention, a strain *Bacillus mycoides* RLJ B-017 is used which can accumulate PHB at higher levels that previous methods and which can utilize minimal medium containing cheap material like sucrose, molasses, etc. for growing conditions. The carbohydrate utilization system present in *Bacillus mycoides* RLJ B-017 allows sucrose, molasses, pineapple waste, etc. to be used as cheap carbon source for the production of PHB. Molasses is a waste product from sugar processing and is very inexpensive. Similarly pineapple waste from fruit industry is also a waste product from fruit processing industries and is very inexpensive. Experiments show that the strain of *Bacillus mycoides* RLJ B-017 grown in minimal medium containing molasses and has an average yield of PHB of approximately 85% (PHB dry weight/total cell dry weight).

Experiments also show that PHB produced in transformed *E. coli* can be agglomerated with sodium hypochlorite or calcium monohypochlorite hydroxide solutions. To retrieve purified PHB of the structure 1 in large quantities, the transformed *Bacillus mycoides* RLJ B-017 cells are first lysed by mechanical or physical means, such as by sonication, or generic means. The cells are then incubated in an ionic solution, such as 10 millimolar (mM) sodium hypochlorite), which agglomerates the PHB granules. Finally, the aggolomerates are centrifuged from the culture at low speed. Experiments show that nearly all (100%) of the PHB of the structure 1 in culture is agglomerated and recovered by this process. The results are especially significant since the same type of agglomeration is not possible or retrieving PHB of the structure 1 from *A. eutrophus*.

From FIG. 1 of the drawings, it is shown that *Bacillus mycoides* RLJ B-017 accumulates a greater percentage of PHB in a short period of 24 hours. The strain *Bacillus mycoides* RLJ B-017 is available from the Biochemistry Division, Regional Research Laboratory, Jorhat-6, Assam, India.

Experiments were performed which shows that the *Bacillus mycoides* RLJ B-017 strain which could be grown on minimal medium containing sucrose or molasses. Activated sludge sample, from wastewater-treatment plant was appropriately diluted and then spread on YPM-agar plates containing (g $1^{31\ 1}$); yeast extract, 10; bactopeptone, 10; meat extract, 5; NaCl, 5; and agar, 20. The plates were incubated at 30° C. for 72 h. Several colonies appearing on the plates were screened for their PHB production. Isolate RLJ B-017, thus selected was used in this study.

Morphological and taxonomic features of the selected isolate was examined by the established method (Sheath et al, 1986). The results are as shown Table 1 in Example 1.

Organism *Bacillus mycoides* RLJ B-017 was maintained and grown at 30±0.5° C. and maintained at 4° C. by the periodical transfer on YPM-agar slants. The inoculum was grown on nutrient rich medium occupying 20% of the flask volume. The nutrient rich medium consists of (g $1^{-1}$): sucrose, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_47H_2O$, 0.01; and trace-element solution 1 ml $1^{-1}$. Trace-element solution contained (g $1^{-1}$): $ZnSO_47H_2O$, 0.2; $H_3BO_3$, 0.6; $MnCl_2$ $4H_2O$, 0.06; $CoCl_2$ $6H_2O$, 0.4; $CuSO_4 4H_2O$, 0.02; $NaMoO_4.2H_2O$, 0.06. The pH was set at 7.2

The composition of basal culture media used was same as that of the inoculum media except nutrient broth was not added. Overnight grown inoculum was transferred directly in a 3 L bioreactor containing the basal culture media of pH 7.2 with 2% sucrose as carbon source. The temperature of the bioreactor was set between 30–35° C. and its rpm was at 200. The cells were harvested by centrifugation after 24 hours corresponding to the exponential growth, and washed twice with distilled water.

10–25% (v/v) Sodium hypochlorite solution of pH 11 was prepared for processing. The cell pellet after centrifugation was treated with dispersions of sodium hypochlorite and chloroform (1:1 v/v). The treatment time was set between 2–3 hours at 30–35° C. The suspension was then centrifuged at 10000 rpm for 15 minutes at 30° C. Three separate phases were obtained. The lower phase containing PHB dissolved in chloroform was precipitated by adding ethanol. The precipitate was kept at cold (4° C.) for 1 hr. and was recovered by centrifuging at 10000 rpm for 15 min. at 4° C. The pellet obtained was pressed to remove ethanol and dried at 60° C. for 24 hrs.

Utilizing sucrose and molasses as the carbon source for the production of PHB, where the sucrose and molasses are present in minimal medium, will result in considerable cost savings over the prior art practice of using rich medium with glucose for producing PHB. The method will be cheaper to the processes of production of PHB using the prior art of transformed *E. coli, Alcaligenes eutrophus*, or genetically manipulated plant cells because of their high cost involved in their production or commercial source.

The invention has been described in terms of its preferred embodiments where a strain of *Bacillus mycoides* RLJ B-017 has been isolated from waste water treatment plants which can accumulate larger quantities of PHB while using an inexpensive carbon course such as sucrose and molasses for PHB production. However, those skilled in the art will recognize that the invention can be practiced with modification within the spirit and scope of the appended claims.

The following non-limiting examples illustrate the methods of the present invention.

EXAMPLE I

Isolation

Activated sludge sample, from wastewater-treatment plant was appropriately diluted and the spread on YPM-agar plates containing (g $l^{-1}$): yeast extract, 10; bactopeptone, 10; meat extract, 5; NaCl, 5; and agar, 20. The plates were incubated at 30° C. for 72 h. Several colonies appearing on the plates were screened for their PHB production. Isolate RLJ B-017, thus selected was used in this study.

Identification of the Isolated Strain

Morphological and taxonomic features of the selected isolate was examined by the established method (Sheath et.al., 1986). The results are summarized in Table 1.

Organism and Maintenance

*Bacillus mycoides* RLJ B-017, was grown at 30±0.5° C. and maintained at 4° C. by periodical transfer on YPM-agar slants.

Inoculum Preparation

The inoculum was grown on nutrient rich medium occupying 20% of the flask volume. The nutrient rich medium consists of (g $l^{-1}$): sucrose, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_4 7H_2O$, 0.01; and trace-element solution 1 ml $l^{-1}$. The trace element solution contained (g $l^{-1}$): $ZnSO_4 7H_2O$, 0.2; $H_3BO_3$, 0.6; $MnCl_2$ $4H_2O$, 0.06; $CoCl_2$ $6H_2O$, 0.4; $CuSo_4 4H_2O$, 0.02; $NaMoO_4.2H_2O$, 0.06. The ph was set at 7.2.

Cultivation Conditions

The composition of basal culture media used was same as that of the inoculum media except nutrient broth was not added. Overnight grown inoculum was transferred directly in a 3 L bioreactor containing the basal culture media of pH 7.2 with 2% sucrose as carbon source. The temperature of the bioreactor was set between 30–35° C. and its rpm was at 200. The cells were harvested by centrifugation after 24 hours corresponding to the end of exponential growth and washed twice with distilled water.

Chemicals

Nutrient both and all the other chemicals used were obtained from Difco Laboratories and Sigma Chemicals Co, and were of high purity analytical grade. Nutrient broth and all the other chemicals obtained from other commercial sources can also be used.

Processing of Biopolymer

10–25% (v/v) Sodium hypochlorite solution of pH 11 was prepared for processing. The cell pellet after centrifugation was treated with dispersions of sodium hypochlorite and chloroform (1:1 v/v). The treatment time was set between 2–3 hrs, at 30–35° C. The suspension was then centrifuged at 10000 rpm for 15 minutes at 30° C. Three separate phases wee obtained. The lower phase containing PHB dissolved in chloroform was precipitated by adding ethanol. The precipitate was kept at cold (4° C.) for 1 hour and was recovered by centrifuging at 10000 rpm for 15 min. at 4° C. The pellet obtained was pressed to remove ethanol and dried at 60° C. for 24 hrs. Weight of biopolymer obtained is 2.4 g per litre of culture, Molecular weight by viscosity method is 5,05,000 dalton, NMR data: $^1H$ NMR ($CDCl_3$): δ 5.25q (J=6 Hz), 2.60 dd (J=7.5 & 15.6 Hz), 2.45 dd (J=6 & 15.6 Hz), 1.28 d (J=6.33 Hz); $^{13}C$ NMR ($CDCl_3$): δ 18.77 (CH3), 39.86 (CH2), 66.65 (CH—O—), 168.12 (O—C=O). DEPT 135 ($CDCl_3$): δ 18.77 (+), 39.86 (−), 66.65 (+). Elemental analysis: C, 55.38%; H, 7.34%; and N, 0.20%; (PHB from Sigma Chemicals, USA); Mol weight 5,35,000 Dalton and elemental analysis C, 55 64%; H, 7.25%; and N, 0.59%).

EXAMPLE 2

Isolation

Activated sludge sample, from wastewater treatment plant was appropriately diluted and then spread on YPM-agar plates containing (g $l^{-1}$), yeast extract, 10; bactopeptone, 10: meat extract, 5; NaCl, 5; and agar, 20. The plates were incubated at 30° C. for 72 h. Several colonies appeared on the plates and were screened for their PHB production. Isolate RLJ B-017, thus selected was used in this study.

Identification of the Isolated Strain

Morphological and taxonomic features of the selected isolate was examined by the established method (Sheath et. Al, 1986). The results are as shown Table 1 in Example 1.

Organism and Maintenance

*Bacillus mycoides* RLJ B-017, was grown at 30±0.5° C. and maintained at 4° C. periodical transfer on YPM-agar slants.

Ionculum Preparation

The inoculum was grown on nutrient rich medium occupying 20% of the flask volume. The nutrient rich medium consists of (g $l^{-1}$): sucrose, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_47H_2O$, 0.01; and trace-element solution 1 ml $l^{-1}$. The trace element solution contained (g $l^-$): $ZnSO_47H_2O$, 0.2; $H_3BO_3$, 0.6; $MnCl_2$ $4H_2O$, 0.06; $CoCl_2$ $6H_2O$, 0.4; $CuSO_44H_2O$, 0.02; $NaMoO_4.2H_2O$, 0.06. The pH was set at 7.2.

Cultivation Conditions

The composition of basal culture media used was same as that of the inoculum media except nutrient broth was not added. Overnight grown inoculum was transferred directly in a 3 L bioreactor containing the basal culture media of pH 7.2 with 2% molasses as carbon source. The temperature of the bioreactor was set between 30–35° C. and its rpm was at 200. The cells were harvested by centrifugation after 24 hours corresponding to the end of exponential growth, and washed twice with distilled water.

Chemicals

Nutrient broth and all the other chemicals used were obtained from Difco Laboratories and Sigma Chemicals Co. and are of high purity analytical grade. However, Nutrient broth and all chemicals obtained from other commercial sources can also be used.

Processing of Biopolymer

10–25% (v/v) Sodium hypochlorite solution of pH 11 was prepared for processing. The cell pellet after centrifugation was treated with dispersions of sodium hypochlorite and chloroform (1:1 v/v). The treatment time was set between 2–3 hours at 30–35° C. The suspension was then centrifuged at 10000 rpm for 15 minutes at 30° C. Three separate phases were obtained. The lower phase containing PHB dissolved in chloroform was precipitated by adding ethanol. The precipitate was kept at cold (4° C.) for 1 hr. and was recovered by centrifuging at 10000 rpm for 15 min. at 4° C. The pellet obtained was pressed to remove ethanol and dried at 60° C. for 24 hrs. Molecular weight by viscosity method is 5,60,000 dalton, NMR data same as given in Example 1 and that of PHB obtained from M/s. Sigma Chemicals in FIG. 2, Elemental analysis: C, 55.19%; H, 7.29%; and N, 0.19%; (PHB from Sigma Chemicals, USA: Mol weight 5,35,000 Dalton and elemental analysis: C, 55.64%; H, 72.5%; and N, 0.59%).

EXAMPLE 3

Isolation

Activated sludge sample, from wastewater-treatment plant was appropriately diluted and then spread on YPM-agar plates containing (g 1–1): yeast extract, 10; bactopeptone, 10; meat extract, 5; and agar, 20. The plates were incubated at 30° C. for 72 h. Several colonies appeared on the plates were screened for their PHB production. Isolate RLJ B-017, thus selected was used in this study.

Identification of the Isolated Strain

Morphological and taxonomic features of the selected isolate was examined by the established method (Sheath et. Al, 1986). The results are as shown Table 1 in example 1.

Organism and Maintenance

*Bacillus mycoides* RLJ B-017, was grown at 30+0.5° C. and maintained at 4° C. by periodical transfer on YPM-agar slants.

Inoculum Preparation

The inoculum was grown on nutrient rich medium occupying 20% of the flask volume. The nutrient rich medium consists of (g $l^{-1}$): sucrose, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_47H_2O$, 0.01; and trace-element solution 1 ml $l^{-1}$. The trace element solution contained (g $l^{-1}$): $ZnSO_47H_2O$, 0.2; $H_3BO_3$, 0.6; $MnCl_2$ $4H_2O$, 0.06; $CoCl_2$ $6H_2O$, 0.4; $CuSO_44H_2O$, 0.02; $NaMoO_4.2H_2O$, 0.06. The ph was set at 7.2.

Cultivation Conditions

The composition of basal culture ivation conditions media used was same as that of the inoculum media except nutrient broth was not added. Overnight grown inoculum was transferred directly in a 3 L bioreactor containing the basal culture media of pH 7.2 with 2% sucrose as carbon source. The temperature of the bioreactor was not between 30–35° C. and its rpm was at 200. The cells were harvested by centrifugation after 24 hrs. corresponding to the end of exponential growth, and washed twice with distilled water.

Chemicals

Nutrient broth and all the other chemicals used were obtained from Difco Laboratories and Sigma Chemicals Co, and are of high purity analytical grade. However, Nutrient broth and all the other chemicals obtained from other commercial sources can also be used.

Processing of Bio-polymer

10–25% (v/v) Sodium hyopochlorite solution of pH 11 was prepared for processing. The cell pellet after centrifugation was treated with dispersions of sodium hypochlorite and chloroform (1:1 v/v). The treatment time was set between 2–3 hours at 30–35° C. The suspension was then centrifuged at 10000 rpm for 15 minutes at 30° C. Three separate phases were obtained. The lower phase containing PHB dissolved in chloroform was precipitated by adding ethanol. The precipitate was kept at cold (4° C.) for 1 hr. and was recovered by centrifuging at 10000 rpm for 15 minutes at 4° C. The pellet obtained was pressed to remove ethanol and dried at 60° C. for 24 hrs. Molecular weight by viscosity method was similar to mentioned above. NMR data were similar to shown in Example 1 and comparison of $^1H$ NMR spectra with that of PHB obtained from M/s. Sigma Chemicals in FIG. 2, Elemental analysis: similar to mentioned above Examples 1 and 2.

TABLE 1

Morphological and taxonomical properties of *Bacillus mycoides* RLJ B-017

| Characterization | Sample bacteria | Characterization | Sample Bacteria |
|---|---|---|---|
| Morphology | | Biochemical properties | |
| Cell shape | Rod | Citrate utilization | – |
| Cell size (μm) | (1.0–1.2 μm × 3.0–5.0 μm) | Urease production | + |
| Motility | – | Methyl red | – |
| Spore position | Central | Voges proskauer | + |
| Spore shape | Ellipsoidal | Nitrate reduction | + |
| Parasporal crystal | – | Casein hydrolyzate | + |
| Gram Staining | + | Acid production from | + |

TABLE 1-continued

Morphological and taxonomical properties of *Bacillus mycoides* RLJ B-017

| Characterization | Sample bacteria | Characterization | Sample Bacteria |
|---|---|---|---|
| Endospore | + | Glucose, Maltose, Trehalose | + |
| Cultural Characteristics | | Galactose, Sucrose, Fructose | + |
| Colony shape | Rhizoid | Mannitol, Arabinose, Xylose | − |
| Optimum temperature | 30° C. | Utilization of | |
| Optimum pH | 7.0 | Rhamnose, Inositol, Ribose | + |
| Growth on nutrient agar | + | Galactose, Histidine, Sucrose | + |
| Growth on MacConkey agar | − | Mannitol, Xylose, Arginine | + |
| Growth at nutrient broth | | Arabinose, Raffinose | + |
| pH 5.0–7.0 | + | Salicin, Serine, Methionine | − |
| pH 8.0 | − | Glycerol, Proline | − |
| Growth at NaCl | | Phenylalanine | − |
| 2.5–7.0% | + | | |
| 8.5% | − | | |
| Growth at 5–20° C., and 50° C. | − | | |
| 25–40° C. | + | | |

We claim:

1. A process for the isolation of polyhydroxybutyrate of formula 1

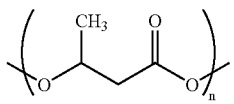

formula 1 said process comprising the steps of:
(a) growing a culture of *Bacillus mycoides* RLJ B-017 bacteria on a growth medium comprising a carbon source selected from the group consisting of sucrose, molasses and pineapple waste for a period of time sufficient to produce the polyhydroxybutyrate of formula 1;
(b) lysing the bacteria in the culture to release the polyhydroxybutyrate of formula 1; and
(c) isolating the polyhydroxybutyrate of formula 1.

2. The process as claimed in claim 1, wherein the culture is grown on the growth medium for a time period equal to or greater than twenty four hours.

3. The process as claimed in claim 2, wherein the growth medium comprises sucrose.

4. The process as claimed in claim 1, wherein said growth medium comprises (g $l^{-1}$): sucrose, 20; nutrient broth, 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_4.7H_2O$, 0.01; and trace-element solution, said trace element solution comprising (g $l^{-1}$): $ZnSO_4.7H_2O$, 0.2; $H_3BO_3$, 0.6; $MnCl_2.4H_2O$, 0.06; $CoCl_2.6H_2O$, 0.4; $CuSO_4.4H_2O$, 0.02; $NaMoO_4.2H_2O$, 0.06; said growth medium having a pH of 7.2.

5. The process as claimed in claim 2, wherein the growth medium comprises molasses.

6. The process as claimed in claim 1, wherein said growth medium comprises (g–$1^{-1}$); molasses, 20; nutrient broth 8; $KH_2PO_4$, 1.5; $(NH_4)_2SO_4$, 2.0; $Na_2HPO_4.12H_2O$, 2.239; $MgSO_4.7H_2O$, 0.2; $CaCl_2.2H_2O$, 0.02; $FeSO_4.7H_2O$, 0.01; and a trace element solution, said trace element solution comprising (g $1^{-1}$): $ZnSO_4.7H_2O$, 0.2; $H_3BO_3$, 0.6; $MnCl_2.4H_2O$, 0.06; $CoCl_2.6H_2O$, 0.4; $CuSO_4.4H_2O$, 0.02; $NaMoO_4.2H_2O$, 0.06, said growth medium having a pH of 7.2.

7. The process as claimed in claim 2, wherein the growth medium comprises pineapple waste.

8. The process as claimed in claim 1, wherein said growth medium comprises (g$l^{-1}$): pineapple waste, 20; nutrient broth, 8; $KH_2PO_4$, 1.5; $(NH_4)_2SO_4$, 2.0; $NaHPO_4.12H_2O$, 2.239; $MgSO_4.7H_2O$, 0.02; $CaCl_2.2H_2O$, 0.02; $FeSO_4.MH_2O$, 0.01; and a trace-element solution, said trace element solution comprising (g$l^{-1}$): $ZnSO_4.7H_2O$, 0.2; $H_3BO_3$, 0.6; $MnCl_2.4H_2O$, 0.06; $CoCl_2.6H_2O$, 0.4; $CuSO_4.4H_2O$, 0.02; $NaMoO_4.2H_2O$, 0.06; said growth medium having a pH of 7.2.

9. The process as claimed in claim 2, comprising pelletizing the isolated polyhydroxybutyrate of formula 1 to form a cell pellet and treating the cell pellet with an ionic reagent comprising a dispersion of a metal hypochlorite in a halogenated hydrocarbon solvent to agglomerate the polyhydroxybutyrate of formula 1.

10. The process as claimed in claim 9, wherein the metal hypochlorite is selected from the group consisting of sodium hypochlorite and calcium hypochlorite.

11. The process as claimed in claim 9, wherein the halogenated hydrocarbon solvent comprises chloroform.

12. The process as claimed in claim 9, wherein the concentration of said ionic reagent is in the range of one molar to one millimolar.

13. The process as claimed in claim 2, wherein the polyhydroxybutyrate of formula 1 is isolated by centrifugation to obtain a plurality of separate phases, including a lower phase comprising the polyhydroxybutyrate of formula 1; dissolving the polyhydroxybutyrate of formula 1 in chloroform and adding ethanol to form a precipitate.

14. The process as claimed in claim 13, wherein the precipitate is chilled and recovered by further centrifuging to recover the polyhydroxybutyrate of formula 1.

* * * * *

UNITED STATES PATENT AND TRADEMARK OFFICE
CERTIFICATE OF CORRECTION

| | |
|---|---|
| PATENT NO. | : 7,129,068 B2 |
| APPLICATION NO. | : 10/613532 |
| DATED | : October 31, 2006 |
| INVENTOR(S) | : Manobjyoti Bordoloi et al. |

Page 1 of 1

It is certified that error appears in the above-identified patent and that said Letters Patent is hereby corrected as shown below:

On title page, insert -- Related U.S. Application Priority Data (62) Continuation of application No. 09/820,188, filed March 28, 2001, now abandoned --.

Col. 1, line 4, insert -- This application is a continuation of copending application number 09/820,188 filed on March 28, 2001, claims the benefit thereof and incorporates the same by reference. --

Signed and Sealed this

Sixth Day of March, 2007

JON W. DUDAS
*Director of the United States Patent and Trademark Office*